United States Patent [19]

Kreizman et al.

[11] Patent Number: 4,634,419
[45] Date of Patent: Jan. 6, 1987

[54] ANGULATED ULTRASONIC SURGICAL HANDPIECES AND METHOD FOR THEIR PRODUCTION

[75] Inventors: Alexander Kreizman, Stamford, Conn.; Alan Broadwin, Brooklyn, N.Y.

[73] Assignee: Cooper LaserSonics, Inc., Santa Clara, Calif.

[21] Appl. No.: 808,573

[22] Filed: Dec. 13, 1985

[51] Int. Cl.⁴ ............................................. A61B 17/20
[52] U.S. Cl. ..................................... 604/22; 128/24 A
[58] Field of Search ................. 128/24 A, 303 R, 305; 604/22, 30, 35-36

[56] References Cited

U.S. PATENT DOCUMENTS

| | | | |
|---|---|---|---|
| 3,546,498 | 12/1970 | McMaster et al. | 310/8.2 |
| 3,693,613 | 9/1972 | Kelman | 128/24 A |
| 4,169,984 | 10/1979 | Parisi | 128/24 A X |
| 4,526,571 | 7/1985 | Wuchinich | 128/24 A X |

Primary Examiner—Kyle L. Howell
Assistant Examiner—Francis J. Jaworski
Attorney, Agent, or Firm—Vorys, Sater, Seymour and Pease

[57] ABSTRACT

An improved ultrasonic surgical handpiece includes an angled connecting body between the transducer and operative tip, with the connecting body being bent at a location between the node and antinode at its respective ends and with a second nodal plane support in the transducer section. The vibrating assembly is impedance matched to the frequency of a handpiece employing a straight connecting body of subtantially equal length and dimension whereby straight and angulated handpieces may be interchangeably used in an ultrasonic surgical system employing a common drive and common operative tips. In a preferred embodiment, the ultrasonic transducer has a nodal plane midway between its ends and is supported at this nodal plane.

7 Claims, 8 Drawing Figures

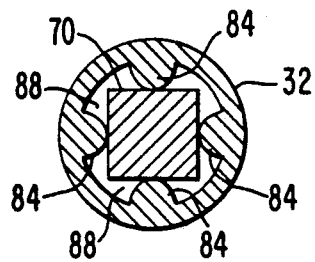
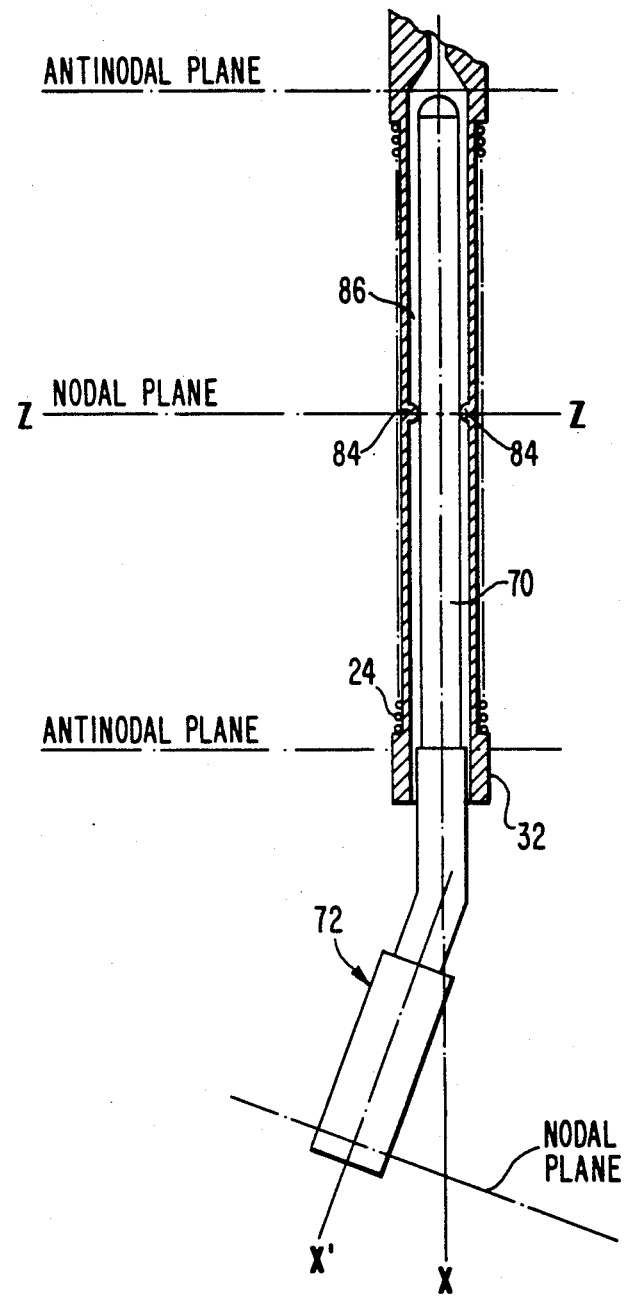

ANGULATED ULTRASONIC SURGICAL HANDPIECES AND METHOD FOR THEIR PRODUCTION

BACKGROUND OF THE INVENTION

1. Field of the Invention

This invention relates to ultrasonic surgical instruments useful in removing tissue from within a biological structure, and more particularly to an improved ultrasonic surgical handpiece employing a transducer and an angled connecting body, and to an improved method of producing such an instrument.

2. Description of the Prior Art

Ultrasonic surgical instruments, generally referred to as handpieces, first met acceptance for use in eye surgery, particularly in the removal of cataracts, and presently are widely used for various surgical procedures. The known ultrasonic handpieces generally employ piezoelectric or magnetostrictive transducers capable of transforming high frequency electrical energy into mechanical impulses or vibrations and essentially consist of an elongated transducer having one end rigidly joined, as by brazing or welding, to an elongated connecting member which, in turn, supports an elongated operative probe or tip on its other end. The vibrating electromechanical assembly, including the transducer, connecting member and probe, are supported by a housing through connecting means which isolates the housing from the mechanical vibrations and provides connections for cooling fluid for the assembly and electrical energy to drive the transducer. Known ultrasonic handpieces of this general type are disclosed, for example, in U.S. Pat. Nos. 3,693,613 and 3,805,787.

The known ultrasonic handpieces in which the operative probe extends coaxially with the housing generally are constructed as $\frac{3}{4}\lambda$ transducers, i.e., the length of the transducer and connecting member constitute $\frac{3}{4}$ of a wavelength, and a matched $\frac{1}{4}\lambda$ tip operative probe mounted on the connecting member completes the full wavelength, with the tip connecting plane being at or closely adjacent to the nodal plane. While these ultrasonic handpieces are widely used in the surgical theatre, their straightline design limits their utility for certain procedures. For example, when the operative site is deep within a biological body, good visibility is not always possible since the housing and the surgeon's hand supporting the housing may interfere with the line of sight to the operative tip. Also, such prior art straight ultrasonic handpieces are of particularly limited utility in microsurgery because the handpiece and the surgeon's hand interfere with the operating microscope.

One attempt to provide an ultrasonic surgical handpiece to overcome the difficulties of the straight handpieces described above is disclosed in U.S. Pat. No. 4,526,571. In this prior art device, a conventional straight transducer assembly is employed to the conventional nodal point mounting for the operative tip, but a $\frac{1}{2}\lambda$ curved extension is inserted between the operative probe and its conventional mounting point to provide in effect, a $\frac{3}{4}\lambda$ extension in which the longitudinal axis of the operative tip is displaced at an angle, for example, 15°, from the longitudinal axis of the transducer assembly. This assembly has successfully solved the problem of visibility at the operative site when working in a deep, restrictive access body opening, but the added length of the overall assembly may reduce the ability of the device to be used in conjunction with an operating microscope in certain conditions. Further, some surgeons accustomed to handling the shorter straight handpieces find it difficult to interchange the longer handpiece because of the difference in maneuverability and balance. Thus, there remains a need for an improved surgical handpiece designed to provide improved visibility at the operative tip and to provide minimal interference with an operating microscope.

It is also known that longitudinal ultrasonic vibrations may be transmitted through an elongated member made up of alternate straight and curved or bent sections. For example, U.S. Pat. No. 3,546,498 discloses a transmission line made up of a series of straight segments joined by short radius bends located at critical locations, i.e., the nodes or antinodes in the transmission element.

A primary object of the present invention is to provide an improved ultrasonic surgical handpiece which overcomes the shortcomings of the prior art handpieces discussed above.

Another object is to provide an improved angled ultrasonic surgical handpiece which is shorter and more maneuverable than the known curved handpieces.

Another object is to provide such an ultrasonic surgical handpiece employing a connecting body which is bent at a location between the nodal and anti-nodal planes adjacent to its ends whereby the axis of the operative tip is disposed at an angle with respect to the axis of the transducer.

Another object is to provide such an ultrasonic surgical handpiece having an improved balance in the surgeon's hand and which is therefore more maneuverable and less fatiguing in use.

Another object is to provide such an improved ultrasonic surgical handpiece for use in connection with operating microscopes and which will not substantially interfere with the use of such microscopes when using at least a 300 millimeter objective lens.

Another object is to provide such an ultrasonic handpiece in which the operative tip and drive components of compatible straight and angled handpieces may be interchanged.

Another object of the invention is to provide a means for producing an angled ultrasonic surgical handpiece which is sufficiently short to be both maneuverable and less fatiguing in the surgeon's hand while not substantially interfering with the use of an operating microscope, and in which a $\frac{1}{4}\lambda$ operative tip of a compatible straight handpiece may be employed.

SUMMARY OF THE INVENTION

In the attainment of the foregoing and other objects and advantages of the invention, an important feature resides in providing an improved angulated ultrasonic surgical handpiece which may be used interchangeably with known straight handpieces by operating room personnel with a minimum of confusion. The handpiece is designed to plug into and operate with commercially avaiable compatible console systems of corresponding frequency and to function with existing surgical tips supplied for use with such commercially available compatible straight handpieces. This is accomplished by providing a connecting member bent at an angle to the longitudinal axis of the transducer at a point intermediate the connector body ends, i.e., between the nodal and antinodal planes at the ends of the connecting body, and by impedance matching the angled transducer to the compatible straight transducer and to the interchangeable tip at the desired operating frequency. To accomplish this, the angled and straight connecting bodies are constructed of the same axial length, and a portion of the mass of the angled connector body is removed at or near the nodal plane, i.e., near the point of connection of the operative tip. Preferably, this material is removed by milling flats from two opposite sides of the connector body, with the flats lying in planes parallel to the plane containing the longitudinal axes of the straight and angled portions of the connecting body.

BRIEF DESCRIPTION OF THE DRAWINGS

The foregoing and other features and advantages of the invention will be apparent from the detailed description contained hereinbelow, taken in conjunction with the drawings, in which:

FIG. 7A is a partial elevation view in partial cross section of the angled handpiece of this invention showing the support means located at the nodal plane.

FIG. 7B is a cross section of the embodiment of FIG. 7A at the nodal plane Z—Z.

DESCRIPTION OF THE PREFERRED EMBODIMENT

Figure 1:
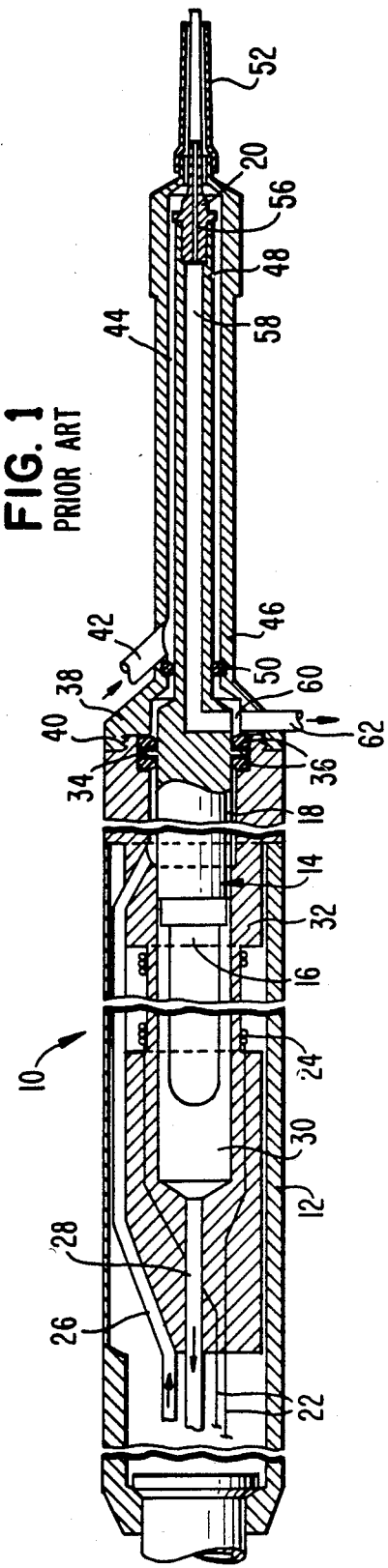
FIG. 1 is a longitudinal sectional view of a prior art straight ultrasonic surgical handpiece over which the present invention is an improvement.

Referring now to the drawings in detail, FIG. 1 shows an ultrasonic aspirator of the general type illustrated, for example, in U.S. Pat. No. 3,693,613, still widely used in surgical practice and over which the present invention is an improvement. The ultrasonic surgical handpiece is indicated generally by the reference numeral 10 and includes a housing member 12 enclosing and supporting the vibration-inducing assembly indicated generally by the numeral 14. Assembly 14 includes a magetostrictive transducer element 16 and an amplifying or connecting member or body 18 having a removable operative tip 20 mounted on its distal end. High frequency electrical energy to drive the transducer is provided through conductors 22 connected to a coil 24 surrounding the transducer 16 within the housing 12. Cooling fluid is circulated through the housing by way of inlet and outlet conduits 26, 28, respectively.

The vibrating body assembly 14 is mounted within the cavity 30 of a support element 32 which, in turn, is mounted on the end of and projects into the housing 12. A pair of resilient gasket members 36 disposed one on each side of a radially extending flange 34 support and effectively isolate the element 32 and housing 12 from vibrations induced by the assembly 14.

An irrigation and aspiration fluid housing 38 is mounted on the end of support element 32 as by threaded connection 40, and retains the resilient gasket members 36 firmly in position. A fluid inlet 42 communicates with a cylindrical fluid chamber 44 between the hollow cylindrical body portion 46 of the housing 38 and the outer surface of the elongated tubular portion 48 of the connecting member 18. A resilient O-ring seal 50 is provided between members 46 and 48 to prevent the flow of irrigation fluid toward the handpiece. A removable sleeve member 52 is mounted on the distal end of housing 38 and extends in surround relation to the operative tip 20.

An aspiration passage 56 extends longitudinally through probe 20 from its free end and communicates with an axial passage in the elongated tubular portion 46 of the connecting body 18. Passage 58 has an outlet communicating with a chamber 60 within housing 38 between the O-ring seal 50 and the gasket seal members 46, and an outlet conduit 62 communicating with the chamber 60 is connected to a source of vacuum for aspirating irrigation fluid and emulsified tissue from the operative site.

The basic construction and operation of the ultrasonic surgical handpiece according to the present invention is substantially similar to the prior art device just described with the exception of the configuration of the vibration-inducing assembly and accordingly only the vibrating components of the ultrasonic surgical handpiece of the present invention are illustrated in the drawings and described herein.

Figure 2:
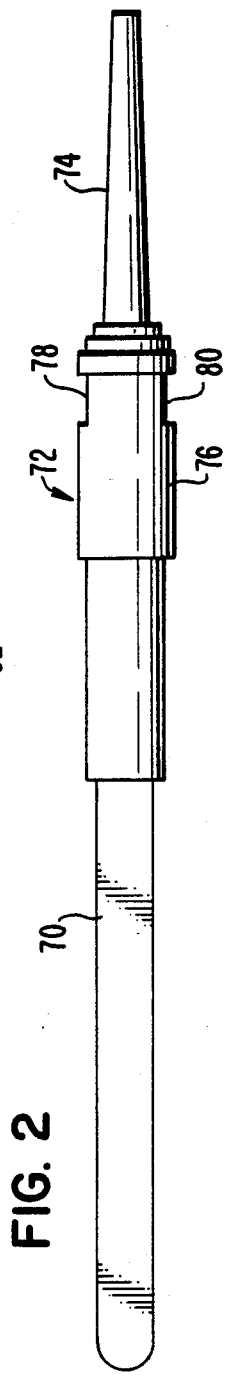
FIG. 2 is a plan view, partially in section, of the transducer assembly and operative tip portion of an ultrasonic surgical handpiece embodying the present invention.
Figure 3:
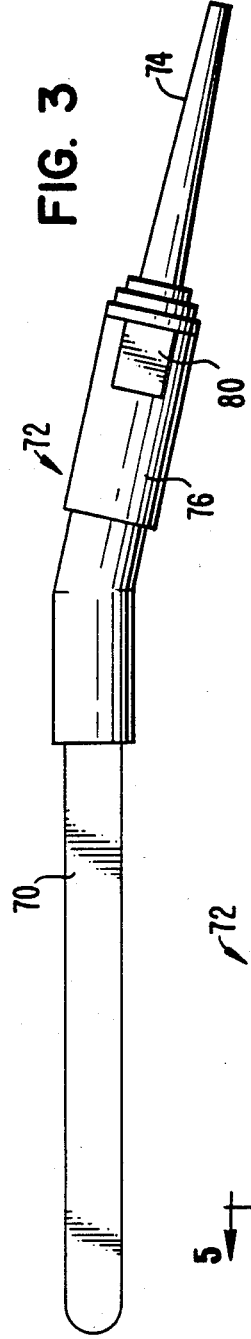
FIG. 3 is an elevation view of the apparatus shown in FIG. 2.
Figure 5:
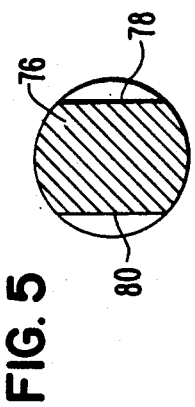
FIG. 5 is a sectional view taken on line 5—5 of FIG. 4.
Figure 4:
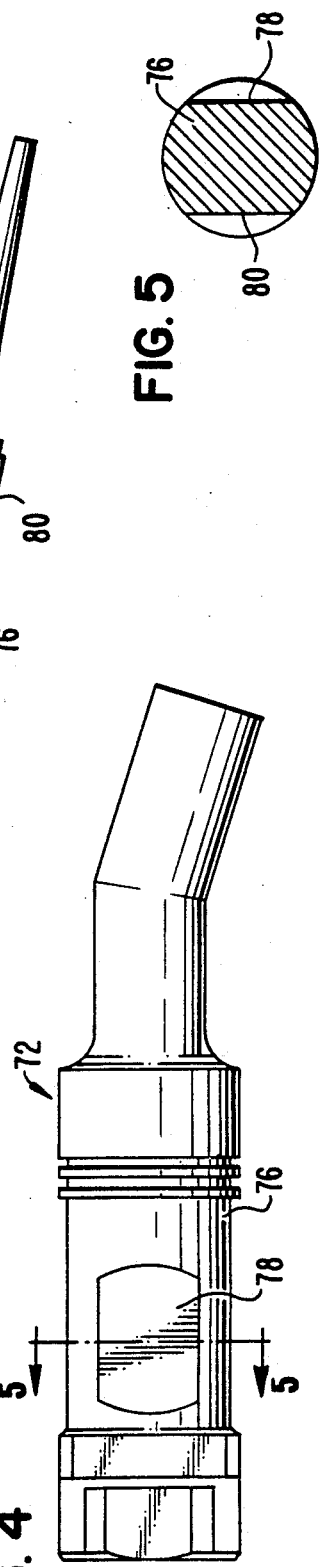
FIG. 4 is an enlarged elevation view of the connector body portion of the apparatus shown in FIG. 3.

Referring initially to FIG. 2, in accordance with the preferred embodiment of the invention, the vibrating structure 68 includes a magnetostrictive transducer element 70 rigidly mounted on and supported by a transmitter element or connecting body 72 adapted to be mounted in a support element and housing in the manner described above. The magnetostrictive element 70 and connecting body 72 together make up a $\frac{3}{4}\lambda$ transducer assembly, and a $\frac{1}{4}\lambda$ operative tip 74 is mounted on the opposite end of the connecting body to complete the full wavelength, with the connection between the tip and connecting body being at or close to the nodal plane. Whether a straight transducer assembly as illustrated in the prior art apparatus of FIG. 1 or the angled assembly shown in FIGS. 2–6, the transducer is designed to vibrate at a predetermined resonant frequency when a properly designed operative tip is attached to the connecting body.

In order to enable a particular operative tip to resonate along its longitudinal axis at the same frequency whether mounted on a transducer assembly including a straight or an angled connecting body, the transducers must be impedance matched to the tip at the desired or designed frequency for the tip. In practice, for a tip designed to resonate at a frequency F, there is a window of frequencies extending above and below the designed frequency in which the assembly will successfully operate. This window of frequencies may be stated as $2\Delta F$, or $F \approx F_o \pm \Delta F$, and thus the ultrasonic generator, or driving unit, is designed to drive the transducer at frequencies within the window $F_o \pm \Delta F$.

If an angled transducer connecting element is constructed by, in effect, bending the straight connecting body, and if the operative tip resonates at a frequency F with a straight transducer, the tip mounted on the angled connecting body will operate at a different frequency F', and the change in frequencies is the same as if the straight connecting body were made shorter.

Figure 6:
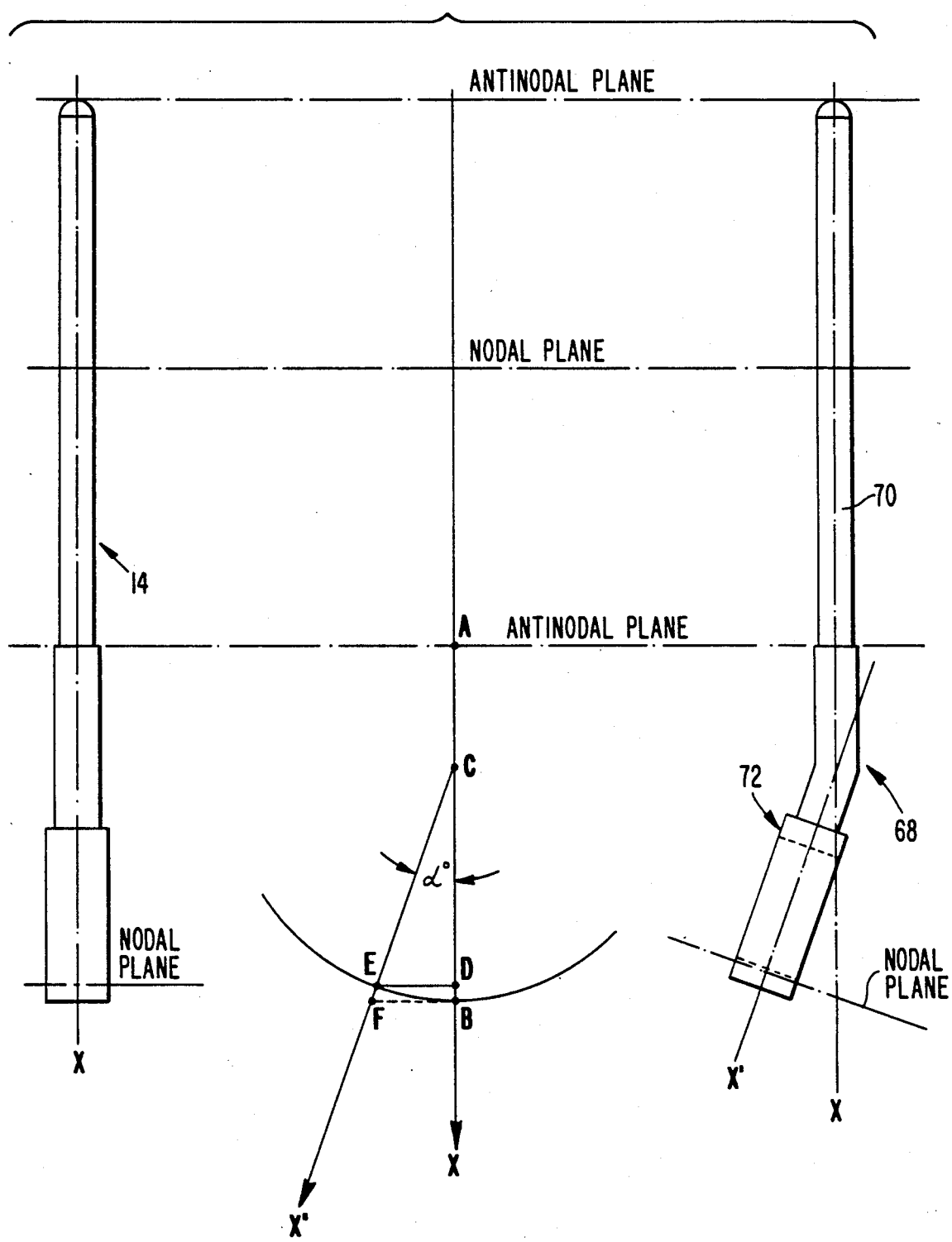
FIG. 6 is a composite view showing the longitudinal axes of a straight and an angled handpiece superimposed.

Referring to FIG. 6 the longitudinal central axis X of a straight transducer and the longitudinal axis X' of the angled portion 76 of a transducer in accordance with the present invention are superimposed, with axis X' intersecting axis X at point C and being disposed at an angle α with respect thereto. Note that the end of the connecting end straight member 18 is connected to the transducer 16 at the second antinodal plane, the first antinodal plane being at the opposite or rear end of the transducer element 16. A first nodal plane is located intermediate the first and second antinodal planes at approximately the midpoint of the magnetorestrictive transducer element, and the second nodal plane is adjacent the end of the connecting body.

As shown in FIG. 6, the superimposed longitudinal central axes of the straight connecting body 18 and the angled connecting body 72 are located at the first antinodal plane indicated at point A. In accordance with the present invention, the connecting body of the angled handpiece is made to resonate along the axis X' which extends at an angle α to the axis X of the straight handpiece, with both transducers being designed to use the same operative tip. If the central longitudinal axis of the straight and angled connecting bodies are the same length, the straight transducer assembly will resonate at a frequency F, while the angled transducer assembly will resonate at a frequency F'. The frequency F' corresponds to the frequency of a shorter straight connecting body.

In FIG. 6, AB represents the overall length of the straight connecting member and AD represents the distance from the antinodal plane at A, to the nodal plane adjacent the free end of the straight connecting member. Point C represents the point of intersection of axes X and X', and point E represents the end of the angled connecting member along axis X'. From the drawings, it is seen that AB=AC+CE×cos α=AC+AD. Thus, the effective length AD of the angled connecting member is less than the length AB of the straight connecting member, and the natural frequency F' of the angled connecting member is therefore greater than the frequency of the straight connecting member.

As is known, the vibrating acoustic elements of ultrasonic surgical handpieces are usually supported at or close to the nodal plane to minimize the power dissipation. If the mechanical design is such as to provide an acoustic assembly vibrating at a resonant frequency F, and this frequency is changed, the location of the nodal points are also changed with a consequent increase in power dissipation and drop in efficiency. However, as previously stated, systems of this type generally are designed to operate within a narrow window of frequencies extending above and below the optimized frequency $F_o$, i.e., an acceptable operating frequency F=optimum $F_o \pm \Delta F$. Within this window of frequencies, efficiency remains substantially constant for practicable purposes but outside the window, stability of the driving generator is unpredictable.

In order to match the frequency of angled and straight connecting bodies to enable both straight and angled handpieces to be used interchangeably with a given system and operative tip, it has been found that the angled transducer can be matched to the tip frequency F without changing its length ACE in FIG. 6. This is accomplished in accordance with the present invention by removing a calculated amount of mass of the angled portion 76 of connecting member 72 adjacent the nodal plane, preferably by milling corresponding flats 78, 80 on diametrically opposite surfaces of the connecting body which are otherwise substantially circular in cross section throughout their length. The flats preferably lie in planes parallel to the plane containing the longitudinal axes of the angles and straight portions of the connecting bodies. The amount of mass and the configuration of the milled portions may be calculated by solving the following equation:

$$(\rho S dx) \frac{\partial^2 \xi}{\partial t^2} = \frac{SY \partial^2 \xi}{\partial x^2} dx$$

wherein
ρ=Volume density
S=Cross-sectional area
(ρSdx)=Represents the mass of fraction dx
ξ=Displacement
Y=Young's modulus An exact solution to the above equation is extremely involved and the practical solution requires many approximations to be taken for placing the proper boundary conditions for mass loaded vibrating bars. In practice, the solution may be achieved with only a few trial and error attempts, according to the following calculation for approximating the mass to be removed:

$$M \approx \left[ \frac{2\pi D^2}{4} \rho \right] [CB - CB \cos \alpha]$$

wherein
D=Diameter of the connecting body at the nodal plane
ρ=Volume density of the connecting body material
CB=Length of the angled portion Utilizing this method, an angled connecting body having the same length as a straight connecting body may be designed to resonate along its axis X' at the same frequency as the straight connecting body, with the bend or angle in the connecting body being located at a point intermediate the node and antinode planes. As indicated previously, acoustic vibrators normally are designed straight to the nodal support point to thereby allow direct axial vector forces to be transmitted along the acoustic vibrator and into the amplifying tip. Bending, if employed, of such acoustic vibrators has therefore normally been accomplished at or after the nodal point support as taught in the above-mentioned Pat. No. 3,546,498.

Bending of an acoustic vibrator behind the support nodal plane (Y—Y) normally results in excessive acoustic vibrator losses accompanied by a shift in operating frequency of the acoustic assembly.

The losses are due, in large part, to the non-axial loading created by the bent portion of the connecting body. The non-axial load creates a force vector which has a radial as well as an axial component. It is the radial component which is unwanted. The losses can be minimized in the following ways:

1. By selecting a lower operating stroke of the operative tip, as long as the selected level is suitable for the surgical procedure desired.
2. By controlling the unwanted lateral motion of the stack, as long as the control means does not interfere with adequate cooling water flow.
3. By adjusting the mass impedance of the connecting body as long as the mechanical fits allow a surgically useful shape.

Thus, a longfelt need for an instrument enabling the use of ultrasonic surgical handpieces in delicate operations involving operating microscopes has been supplied. In addition, the apparatus enables the use of existing drive equipment and operative tips whereby operating room personnel can readily interchange the angled handpiece and conventional straight handpieces without undergoing extensive training or retraining.

In a preferred embodiment of the invention illustrated schematically in FIG. 7A and FIG. 7B the magnetostrictive transducer 70 is held firmly in a support means located at the nodal plane Z—Z which tightly clamps the laminated transducer 70. In the illustrated embodiment the support means comprises radially inwardly directed projections 84 on the inner wall 86 of the support element 32. The support means includes means for permitting fluid flow therethrough in order to assure an adequate flow of cooling fluid around the transducer 70. In the illustrated embodiment the means for permitting fluid flow comprises apertures 88 between the projections 84.

While a preferred embodiment of the invention has been disclosed and described in detail, it is understood that the invention is not so limited but rather than it is intended to include all embodiments which would be apparent to one skilled in the art and which come within the spirit and scope of the invention.

What is claimed is:

1. In an ultrasonic surgical handpiece for breaking apart and removing tissue from a recessed operative site, the handpiece including a vibration assembly having an elongated straight transducer operable to convert high frequency electrical energy to high frequency mechanical vibrations, an elongated connecting body having one end rigidly joined to one end of the elongated transducer, and an elongated straight operative tip removably mounted on the other end of the connecting body, the vibrating assembly having an overall length substantially equal to the length of the longitudinal vibration wave $\lambda$ when vibrated at the resonant frequency F of the assembly, the vibration wave $\lambda$ having an antinodal plane adjacent to the joined ends of the transducer and connecting body, and a nodal plane adjacent to the other end of the connecting body, the improvement wherein said connecting body comprises,
a first substantially straight portion having a longitudinal axis coincident with the longitudinal axis X of said transducer and a second substantially straight portion having a longitudinal axis X' extending at an angle $\alpha$ with respect to the axis X, said connecting body having a circular cross section throughout at least a major portion of its length and having a portion of its mass removed from its outer surface at a location adjacent to said nodal plane relative to the mass of a straight connecting body of the same cross-section whereby the resonant frequency of the angled vibrating assembly is substantially identical to the resonant frequency of said vibration assembly of equal length and dimension and having said straight connecting body but without the mass removed from the connecting body.

2. The ultrasonic surgical handpiece defined in claim 1 wherein the mass removed from said connecting body comprises a pair of substantially parallel flats milled into diametrically opposite sides of said connecting body.

3. The ultrasonic surgical handpiece defined in claim 2 wherein said flats lie in planes parallel to the plane containing axes X and X'.

4. The ultrasonic surgical handpiece defined in claim 3 wherein the mass removed from said connecting body is determined by the formula:

$$M \approx \left[ \frac{2D^2}{4} \rho \right] [CB - CB \cos\alpha]$$

wherein
D = Diameter of the connecting body at the nodal plane
$\rho$ = Volume density of the connecting body material
CB = Length of the angled portion 5. The ultrasonic surgical handpiece defined in claim 1 wherein said transducer has a nodal plane located midway between its ends and said handpiece further comprises support means located at said nodal plane of said transducer for supporting said transducer.

6. The ultrasonic surgical handpiece defined in claim 5 wherein said support means includes means for permitting fluid flow through said support means.

7. The ultrasonic surgical handpice defined in claim 6 wherein said support means for said transducer comprises radially inwardly directed projections on a support member surrounding said transducer.

* * * * *